United States Patent [19]

Heck

[11] 4,193,137
[45] Mar. 18, 1980

[54] WARP-KNITTED DOUBLE-VELOUR PROSTHESIS

[75] Inventor: Rudolf N. Heck, Ringwood, N.J.
[73] Assignee: Meadox Medicals, Inc., Oakland, N.J.
[21] Appl. No.: 794,481
[22] Filed: May 6, 1977
[51] Int. Cl.$^2$ ............................................. A61F 1/24
[52] U.S. Cl. ............................................. 3/1.4; 3/1; 66/194; 66/195; 66/203
[58] Field of Search ................. 3/1.4, 1; 128/334 R; 66/194–197

[56] References Cited
U.S. PATENT DOCUMENTS

| | | | |
|---|---|---|---|
| 2,978,787 | 4/1961 | Liebig | 3/1.4 |
| 3,096,560 | 7/1963 | Liebig | 3/1.4 X |
| 3,434,306 | 3/1969 | Auville et al. | 66/194 X |
| 4,047,252 | 9/1977 | Liebig et al. | 3/1.4 |

Primary Examiner—Ronald L. Frinks
Attorney, Agent, or Firm—Blum, Kaplan, Friedman, Silberman & Beran

[57] ABSTRACT

A warp-knitted fabric has pile loops on both faces thereof. The loops on both faces are continuous with each other so that when the fabric is used as a prosthesis, growth of tissue from one face to the other is facilitated. This feature is particularly significant when the fabric is fashioned into tubular form, whether straight or bifurcated. The structure of the fabric is such that a desired degree of rigidity is obtained with a thinner fabric than has hitherto been the case.

19 Claims, 7 Drawing Figures

WARP-KNITTED DOUBLE-VELOUR PROSTHESIS

CROSS-REFERENCE TO RELATED APPLICATIONS

The present application is related to the application having the Ser. No. 653,680 entitled A DOUBLE-VELOUR SYNTHETIC VASCULAR GRAFT AND PROCESS OF MANUFACTURING SAME, filed Jan. 29, 1976, and which issued as U.S. Pat. No. 4,047,252 said application being assigned to the same assignee as the present application, and Ser. No. 638,580 entitled CIRCULARLY-CRIMPED TUBULAR PROSTHESIS AND METHOD OF PRODUCING SAME, filed Dec. 8, 1975 and now abandoned. This latter application is also assigned to the same assignee as the present application.

BACKGROUND OF THE INVENTION

In the process of vascular surgery it frequently becomes necessary to replace or bypass a defective vein or artery or portions thereof. A wide variety of materials have been examined and tested as grafts. Examples are bovine and porcine blood vessels, and tubular prosthesis woven or knitted to Teflon and other synthetic fibers.

Blood vessels taken from umbilical cords have recently been disclosed as being highly effective as grafts as well as for other prosthetic applications in that they appear to be completely free of thrombogenicity and antigenicity. However, the umbilical cord vessels are of relatively small diameter, so that tubular prosthesis of these vessels have a maximum internal diameter of about 5 mm. For larger vessels such as the aorta and the aorta in combination with the two iliac arteries, knitted tubular prostheses are best from the standpoint of tissue ingrowth and freedom from thrombogenicity. Furthermore, polyester fiber, and, in particular, polyester fiber manufactured by Dupont and sold under the tradename of Dacron (polyethylene terephthalate appears to be the best fiber.

A number of problems arise in connection with the knitted tubular prostheses. The first problem is that of leakage of blood through the wall of the prosthesis. This problem is met by making the openings in the knitted wall as small as possible and by preclotting the blood of the patient in the wall of the prosthesis. Optimally, all openings in the wall of the prosthesis are closed with clotted blood prior to joining the prosthesis to the vessels of the patient by anastomosis.

In order that the graft should be essentially circular in section, thereby providing for minimum resistance to flow of blood therethrough, it is necessary that the prosthesis be crimped. Sprial crimping which provides an appropriate degree of rigidity to the tubular prosthesis has been disclosed in U.S. Pat. No. 3,945,052 issued Mar. 23, 1976. Circular crimping which provides additional protection against twisting is taught in application Ser. No. 638,580 referred to above.

Once the graft is inserted and the patient is closed up, success of the graft depends upon ingrowth of tissue through the wall of the prosthesis to form an interior which will resemble the vessels into which the graft has been inserted insofar as it serves to provide a lumen for the flow of blood therethrough without causing either thrombosis or rejection.

It has been found that the ingrowth of tissue is facilitated by "roughening" both the interior and the exterior of the tubular prosthesis. Sauvage in German Offenlegungsschrift No. 24 61 370 has disclosed a prosthesis which is circularly knitted and which has a pile velour both interior and exterior to the wall of the prosthesis. Further, the prosthesis crimped, though in an irregular fashion, so that the rigidity of the prosthesis varies along its length.

Sauvage's prosthesis is knitted of at least three threads and preferably four, all of the threads forming portions of the wall, one thread, periodically, being drawn into exterior loops and another thread, also periodically, being drawn into interior loops. As is evident, where one or two threads are used exclusively to form the wall of the prosthesis and the other two threads are used, at least in part, for forming the wall of the prosthesis, the wall of the prosthesis is necessarily relatively thick. Further, the number of loops, both interior and exterior per unit area cannot be maximal since the looped threads are also used for forming the wall of the prosthesis. Since the loops have been found to facilitate the growth of tissue in the prosthesis wall, it is evident that it would be desirable that the number of loops per unit area of wall be as large as possible.

As can be seen, then, it would be desirable that a number of improvements be introduced into the construction of knitted fabric prosthesis, these improvements including smaller openings between the threads, greater number of loops per unit area, thinner fabric taking into account both the wall thickness and the height of the interior and exterior loops, the reduction in thickness to be achieved without increase in porosity or loss of rigidity, and more rapid ingrowth of tissue.

SUMMARY OF THE INVENTION

One or more elongated strips of fabric are warp-knitted using a single thread to form what is termed the "wall" or "trellis" of the fabric and a second thread which passes back and forth through the wall to form loops on both faces of the fabric. These loops constitute a velour or pile and the fabric having loops on both faces thereof is termed a double-velour fabric. The fabric may be used directly as a prosthesis or two such strips are joined together along the edges thereof to form a fabric of tubular structure. The fabric is then crimped, preferably circularly-crimped to provide the desired degree of rigidity. Uniform crimping of the fabric provides uniform rigidity and uniform resistance to kinking.

Preferably, the wall of the fabric is formed of a single thread which may be single-ply, double-ply or multiple-ply. The thread consists of filaments which are first twisted together to form strands. The term "ply" then refers to the number of strands twisted together to form the thread. A single-ply thread, for example, is a single strand thread, and a multiple ply thread has more than two strands. The total count of the thread of the trellis is between about 30 and about 100 denier, and the thread is preferably non-texturized. The total count of the thread forming the pile is between about 30 and about 150 denier and is preferably texturized.

The preferred thread is synthetic polyester and the preferred polyester is that manufactured by Dupont under the tradename of Dacron (polyethylene terephthalate).

To manufacture the pile, the thread forming the pile is fed to the knitting machine at a rate greater than that at which the thread forming the wall is fed. The ratio of the feed rate of the thread for the pile to the feed rate of the thread for the trellis is between 2.2:1 and 1.2:1.

The thread forming the pile passes through the trellis in both directions so that the loops on one face of the trellis are continuous with the loops on the other face of the trellis. Where the prosthesis is tubular, the loops on the exterior (termed the "technical face") of the trellis are continuous with the loops on the interior of the trellis and the ratio of the exterior to interior loops lengths preferably lies between 3:1 and 1:1. The loops on the interior (termed the "technical back") of a tubular prosthesis are formed from the pile underlap and may be termed sub-loose because they are formed in pairs as the result of the presence of a trellis underlap on the interior surface which divides each interior loop (i.e. pile underlap) in two.

Warp-knitting using a flat thread for the trellis and a texturized thread for the loops makes it possible to provide a prosthesis with smaller openings, that is, lower porosity than is the case with circular knitting, and with loops which are continuous from one face of the prosthesis to the other, thereby facilitating growth of tissue through the wall of the prosthesis. Also, where the prosthesis is tubular, greater rigidity is provided for a given thickness of the prosthesis.

The pile is made with an open stitch while the trellis is made with a closed stitch. Also, the underlapping of pile and trellis threads is in opposite directions.

Accordingly, an object of the present invention is a prosthesis having finer openings than hitherto available, with pile loops on both surfaces of said prosthesis and with a degree of rigidity greater than available with a circular-knitted prosthesis of the same thickness.

Another object of the present invention is a warp-knitted prosthesis which can readily be formed into a tubular structure, both straight and bifurcated.

A further object of the present invention is a warp-knitted prosthesis which facilitates growth of tissue from one face thereof to the other.

Yet another object of the present invention is a warp-knitted prosthesis of the double-velour type in which the trellis thread is in closed stitch and the underlaps are in opposed directions.

An important object of the present invention is a method of warp-knitting a prosthesis wherein a single thread which may have a plurality of plies forms the wall or trellis of said prosthesis and another thread which also may have a plurality of plies passes from one face of said prosthesis to the other thereby making the fabric of said prosthesis a double velour.

A significant object of the present invention is a method of forming a tubular prosthesis of the double-velour type wherein said prosthesis may be bifurcated or straight and said prosthesis has uniform rigidity along each of its limbs.

A vital object of the present invention is a method of forming a double-velour prosthesis wherein the height of the pile on both faces of the prosthesis fabric may be controlled by controlling the ratio of the rate of feed of the thread forming the fabric.

Still other objects and advantages of the invention will in part be obvious and will in part be apparent from the specification.

The invention accordingly comprises the several steps and the relation of one or more of such steps with respect to each of the others, and the product possessing the features, properties, and the relation of components which will be exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1b is a view taken along line 1b—1b of FIG. 1a;

FIG. 1c is a view taken along line 1c—1c of FIG. 1a;

DESCRIPTION OF THE PREFERRED EMBODIMENTS

Figure 1A:
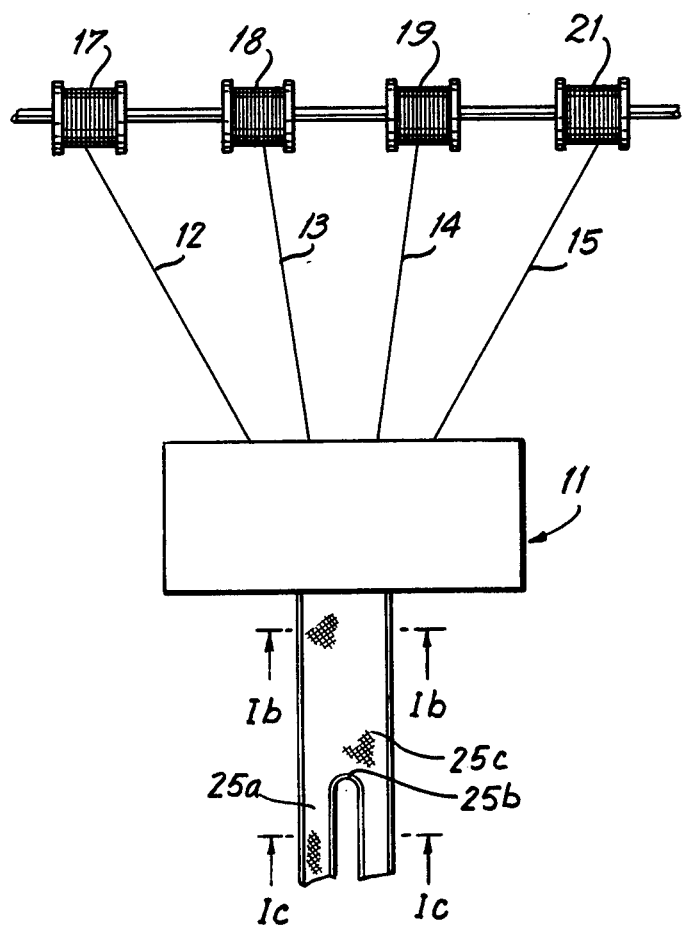
FIG. 1a is a schematic diagram of a warp-knitting machine being fed with thread from four beams and knitting two elongated strips of double-velour fabric for use in a prosthesis.
Figure 1B:
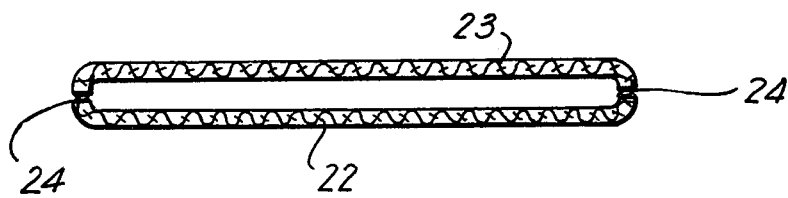
Figure 1C:
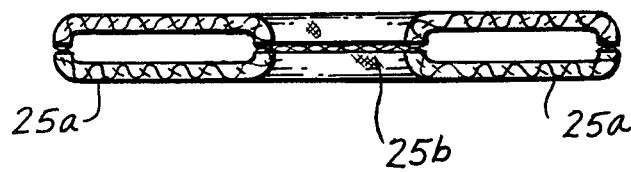

Referring now to FIG. 1, a warp-knitting machine is represented generally by the reference numeral 11. The machine 11 is being fed with threads 12, 13, 14 and 15, respectively, from spools 17, 18, 19 and 21. Machine 11 as shown in FIG. 1 is simultaneously warp-knitting two elongated strips of fabric 22 and 23. The fabric is carried forward by a conveyor belt (not shown). Threads 12 and 13 are processed by machine 11 into fabric strip 22 and threads 14 and 15 are similarly processed into fabric strip 23. Threads 12 through 15 are preferably of polyester and best results have been achieved where the polyester is of Dacron, manufactured by Dupont Company.

In a preferred form, one thread of each pair is flat and is knitted by machine 11 to form the wall or trellis of the fabric. The other thread of each pair preferably texturized and is passed back and forth through the wall of the fabric strip to form pile loops on both sides of the trellis of the fabric. The loops on both sides of the fabric are therefore continuous with each other. The feed rate of the thread which forms the loops is greater than the feed rate of the thread which forms the trellis of the fabric. The ratio of the feed rate of the loop thread to the trellis thread preferably lies between 2.2:1 and 1.2:1. As is evident, the ratio of the length of loops thread in the fabric to trellis thread in the fabric must also lie between 2.2:1 and 1.2:1. The pile may also be referred to as pile velour.

Threads 12 through 15 may be single-ply, double-ply or multi-ply. Preferably, the total count for the trellis thread, whether of one or more plies, is between about 30 and about 100 denier and of the velour thread is between about 30 and about 150 denier.

In the knitting operation the number of needles per inch is from about 18 to about 36 with the preferred number being 28/inch. The fabric, prior to compaction has 35 to 70 courses and 20 to 38 wales per inch. After compaction, the number of courses is from 50 to 100 per inch and the number of wales is 30 to 60 per inch. The fabric may be knitted as a tricot or as locknit (reverse jersey).

Depending upon the vessel which is to be reinforced by a prosthesis in accordance with the present invention, or replaced or by-passed by such a prosthesis, there are applications in which a relatively light fabric is desirable and other applications in which a relatively thick fabric is desirable. For the light fabric, a single ply with a count of about 40 denier is preferred. Such a thread should consists of from 25 to 29 filaments. For the heavy fabric a double-ply thread having a total count of about 80 denier is preferred. Such a thread preferably has 50 to 58 filaments therein. As is evident, fabrics with a single or multi-ply thread having counts anywhere from 30 to 150 denier may be found useful for specific applications.

Figure 3:
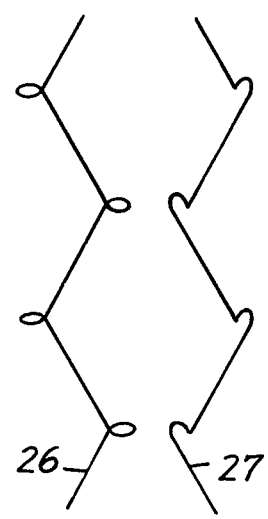
FIG. 3 is a point diagram of the fabric of FIG. 2.
Figure 2:
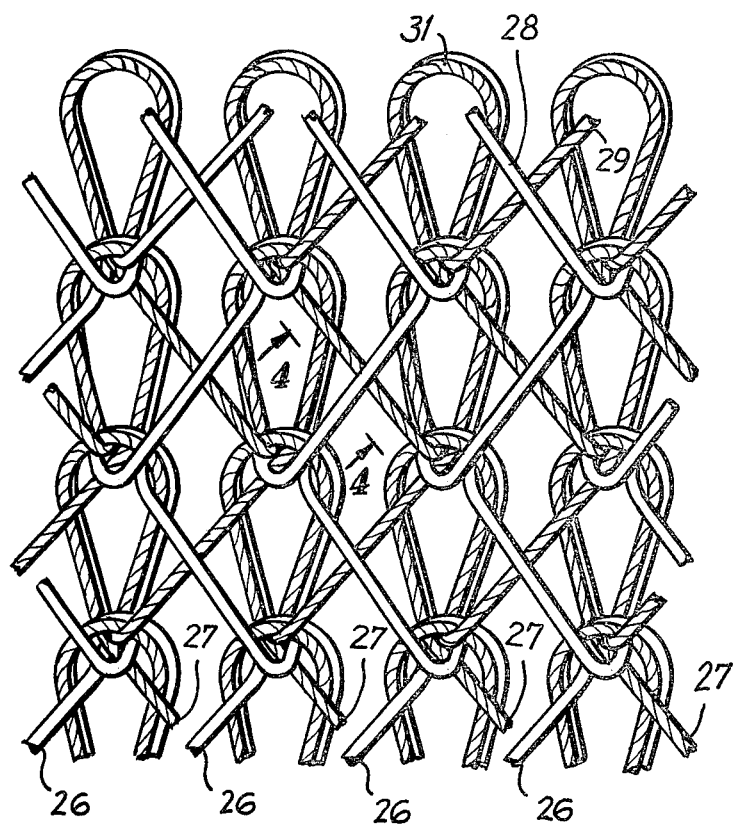
FIG. 2 is a view from the interior of a double-velour fabric showing the relative position of the threads forming the fabric.

In knitting the fabric of the present invention the trellis, indicated by the reference numeral 26, is knitted with a closed stitch whereas the loops 27 are knitted with an open stitch. The point diagram for the warp-knitted fabric of FIG. 2 is shown in FIG. 3. As can be seen, the trellis 26 is knitted with a closed stitch while the loops forming the velour 27 are knitted with an open stitch.

Figure 4:
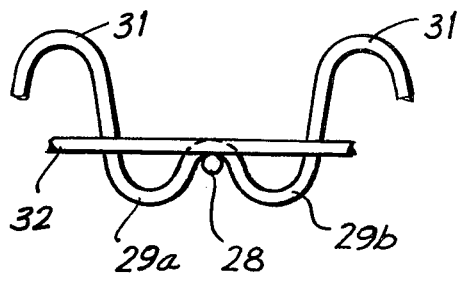
FIG. 4 is a view along line 4—4 of FIG. 2.

Returning to FIG. 2, that portion of the trellis thread indicated by the reference numeral 28 is a trellis underlap with reference to that portion of the pile thread underlap 29 which passes over it (remembering that FIG. 2 is a view of the fabric from the inside thereof). The loop which would be formed by thread underlap 29 is bisected by trellis underlap 28 so that the loop is cut into two sub-loops 29a and 29b as shown in FIG. 4. Underlap 28 dominates because it is relatively tight whereas underlap 29 is loose as the result of the feed ratio being greater than 1. As a result, there are two loops on one face of the fabric, here the interior thereof, for each loop on the exterior of the fabric.

As is evident, underlaps 28 and 29 are in opposite directions. It is possible to form a double velour with the underlaps in the same direction, but as can be seen, the pile loops would not be cut in two so that the number of loops on the inside would be the same as that on the outside of the trellis. The hand of such a product is rather different from that of a product made with opposed underlaps but is useful for certain purposes.

The overlap having the reference numeral 31 is shown in FIG. 2 as lying along the trellis, but this representation is schematic only. Loops 31 are shown more accurately in FIG. 4 as extending outwardly from trellis 32.

A major factor in the warp-knit fabric disclosed herein is the difference in the type of stitch used for making the trellis and the pile. The trellis is made with a closed stitch whereas the pile is made with an open stitch. This difference in the type of stitch used provides for the rigidity of the structure whereas the open stitch of the pile provides lower porosity in the structure, more uniform pile, more even appearance and better hand.

By control of warp-knitting machine 11 the ratio of the height of loops 31 to sub-loops 29a and 29b can be controlled. Preferably this range lies between 3:1 and 1:1. The fact that these loops, exterior and interior are continuous with each other facilitates the ingrowth of tissue from the exterior of a tubular prosthesis to the interior thereof and accelerates the conversion of the surface of the prosthesis to one resembling the interior of a normal artery or vein. Also, the interior and exterior loops provide excellent anchorage for the tissue which deposits. It is these properties which are primarily responsible for the excellent results achieved with the double-velour warp-knitted fabric of the present invention.

To warp-knit a tubular prosthesis, threads 12 and 13 are combined to form back strip 22 and threads 14 and 15 are combined to form front strip 23. As the strips 22 and 23 are warp-knit by machine 11, the machine simultaneously knits the two strips together along the elongated edges thereof, the joins between the two strips being indicated by the reference numeral 24. The machine can knit a bifurcated section indicated by the reference numeral 25a. Generally, it is desirable to reinforce the crotch 25b where the bifurcated section 25a joins tubular section 25c. The reinforcement is carried out subsequent to the knitting and is sewn. The joined strips are then brought into essentially cylindrical form and crimped. As aforenoted, it is highly desirable that the crimping be uniform so that the rigidity along the prosthesis is constant. Further, it is also strongly desirable that the crimping be shallow, thereby facilitating shaping of the ends of the prosthesis to conform to openings in vessels to which the prosthesis is to be joined.

Figure 5:
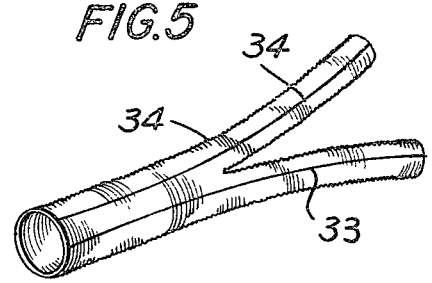
FIG. 5 is a perspective view of a circularly-crimped bifurcated prosthesis.

The crimping may be done in spiral fashion but preferably is circular, since circularly crimped tubular prostheses are free of any tendency to twist when extended. Such twist can increase the danger of kinking. Avoidance of twist during stretching of the prosthesis as is frequently necessary during attachment to other vessels is further facilitated by the use of one or more guidelines 33 as shown in the bifurcated prosthesis 34 in FIG. 5.

The use of the flat thread for the trellis makes it possible to produce a fabric of lower porosity. The use of texturized thread for the velour loops helps to decrease the porosity of the resultant fabric and simultaneously provide better anchorage for tissue during ingrowth. The combination of the two types of thread, a combination which, so far, has not been achieved with any other type of knitting, yields a fabric and tubular prosthesis with an extremely fine hand with appropriate rigidity over a wide range of thicknesses and which conforms excellently after shallow and uniform crimping to the openings in the vessels to which the prosthesis is to be joined. As an example of the range of thicknesses which can readily be provided, the thicknesses being measured before crimping, fabrics ranging from about 0.40 up to about 0.80 mm in thickness can be made on a routine basis. This range is to be regarded as merely exemplary-fabrics of either smaller or greater thickness can undoubtedly be manufactured by the process as described.

It will thus be seen that the objects set forth above, among those made apparent from the preceding description, are efficiently attained and, since certain changes may be made in carrying out the above process and in the product set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. A warp-knitted prosthesis, comprising a trellis, pile velour exterior to said trellis and pile velour interior to said trellis, said pile velour being in the form of loops protruding from said trellis, said trellis consisting of a flat thread of synthetic fiber warp-knitted in closed stitch, and said pile velour consisting of a texturized thread of synthetic fiber in open stitch passing through said trellis to form loops interior to and exterior to said trellis, said interior and exterior loops being continuous with each other for facilitating ingrowth of tissue from the exterior of said prosthesis to the interior thereof, the combination of a trellis warp-knitted of flat thread in closed stitch and a velour of texturized thread in open stitch providing minimum porosity, appropriate rigidity for functioning as a prosthesis and extremely fine hand.

2. The warp-knitted prosthesis as claimed in claim 1, wherein the underlapping of the thread of said trellis is opposed to the underlapping of the thread of said pile velour.

3. The warp-knitted prosthesis as claimed in claim 1, wherein the thread of said trellis is so disposed as to form a trellis underlap with respect to the thread of said pile velour interior to said trellis, said trellis underlap intersecting each of the pile underlap loops interior to said trellis and dividing each of said pile underlap loops into two sub-loops for providing twice as many sub-loops interior to said trellis as loops exterior to said trellis.

4. The warp-knitted prosthesis as claimed in claim 3, wherein the ratio of the length of said exterior loops to said interior sub-loops lies between 3:1 and 1:1.

5. The warp-knitted prosthesis as claimed in claim 1, wherein at least one of said trellis and said pile velour threads is single ply.

6. The warp-knitted prosthesis as claimed in claim 1, wherein at least one of said trellis and said pile threads is of a plurality of plies.

7. The warp-knitted prosthesis as claimed in claim 1, wherein the total count of the thread of said trellis is between about 30 and about 100 denier.

8. The warp-knitted prosthesis as claimed in claim 1, wherein the total count of the thread of said pile velour is between about 30 and 150 denier.

9. The warp-knitted prosthesis as claimed in claim 1, wherein said synthetic fiber thread is of polyester.

10. The warp-knitted prosthesis as claimed in claim 1, wherein said synthetic fiber thread is of polyethylene terephthalate.

11. The warp-knitted prosthesis as claimed in claim 1, wherein said thread is single ply of a count of about 40 denier.

12. The warp-knitted prosthesis as claimed in claim 11, wherein said thread consists of from 25 to 29 filaments.

13. The warp-knitted prosthesis as claimed in claim 1, wherein said thread is double ply with a count of about 80 denier.

14. The warp-knitted prosthesis as claimed in claim 1, wherein said thread has a count of about 80 denier and consists of 50 to 58 filaments.

15. The warp-knitted prosthesis as claimed in claim 1, wherein the ratio of the length of the thread of said pile velour to the length of the thread of said trellis lies between 2.2:1 and 1.2:1.

16. The warp-knitted prosthesis as claimed in claim 1, wherein said prosthesis is tubular in form, each comprising two elongated strips, said strips being joined together at the long edges thereof.

17. The warp-knitted prosthesis as claimed in claim 16, wherein said prosthesis is bifurcated, each comprising a first tubular section and two second tubular sections, said first tubular section being joined at one end thereof to one end of each of said second tubular sections, the join between said first and second sections being free of any gap.

18. The warp-knitted prosthesis as claimed in claim 16, wherein said prosthesis is circularly crimped.

19. The warp-knitted prosthesis as claimed in claim 17, wherein said prosthesis is circularly crimped.

* * * * *